United States Patent [19]

Kobayashi et al.

[11] Patent Number: 4,669,123
[45] Date of Patent: May 26, 1987

[54] INSPECTING METHOD AND APPARATUS FOR PHOTOMASK PATTERN

[75] Inventors: Kenichi Kobayashi, Tokyo; Takayoshi Matsuyama, Kawasaki, both of Japan

[73] Assignee: Fujitsu Limited, Kawasaki, Japan

[21] Appl. No.: 651,086

[22] Filed: Sep. 17, 1984

[30] Foreign Application Priority Data

Sep. 16, 1983 [JP] Japan ................ 58-171811

[51] Int. Cl.⁴ .............................. G06K 9/00
[52] U.S. Cl. ........................ 382/8; 382/21; 382/27
[58] Field of Search ................ 382/8, 21, 27

[56] References Cited

U.S. PATENT DOCUMENTS

| | | | |
|---|---|---|---|
| 3,899,771 | 8/1975 | Saraga et al. | 382/21 |
| 4,148,065 | 4/1979 | Nakagawa et al. | 382/8 |
| 4,490,848 | 12/1984 | Beall et al. | 382/21 |
| 4,532,650 | 7/1985 | Wihl et al. | 382/8 |

FOREIGN PATENT DOCUMENTS 3013833 10/1980 Fed. Rep. of Germany .

OTHER PUBLICATIONS

IBM Technical Disclosure Bulletin, vol. 25, No. 11b, Apr. 1983, pp. 6080–6081, N.Y., J. C. Harmon, "Angular Features for Character Recognition".

Primary Examiner—Howard A. Birmiel
Attorney, Agent, or Firm—Staas & Halsey

[57] ABSTRACT

A method and an apparatus for inspecting a photomask pattern utilizing a vector comparing method. A pair of optical images intended to be compared are taken from the photomask pattern and converted to digital data by optical systems and an amplitude distributor. The digital data have values of black (B), gray (G), or white (W) corresponding to high, middle, and low signal amplitudes. Separated data corresponding to a portion of each of the optical images are sequentially separated from the digital data by data separators. The separated data are shifted by several matrix elements of the separated data by data shifters to provide shifted data. The shifted data of each optical image and separated data are respectively synthesized by data synthesizers to provide two groups of synthesized data. Vectors are generated from the matrices of the groups of synthesized data by vector generators. The vectors are defined to indicate changes from B to W, from B to G, and from G to W, in one of eight latitudinal, longitudinal, and diagonal directions. The number of vectors having the same direction in vectors are respectively summed and compared by a vector comparator which outputs information of a defect on the photomask pattern if there is a difference between the groups for the summation of any vector direction.

13 Claims, 11 Drawing Figures

FIG. 3(a-1).
(PRIOR ART)
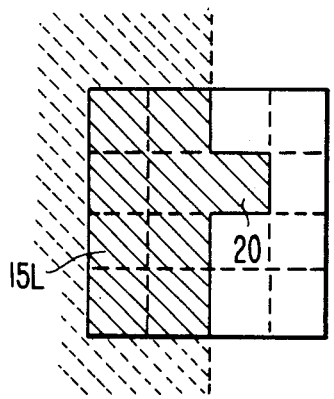
FIG. 3(b-1).
(PRIOR ART)
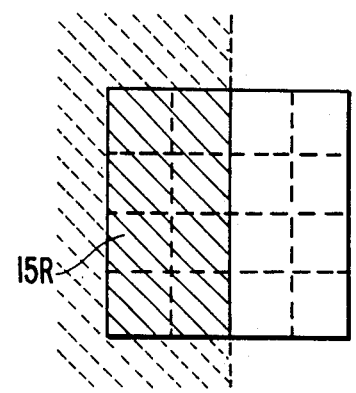
FIG. 3(a-2).
(PRIOR ART)
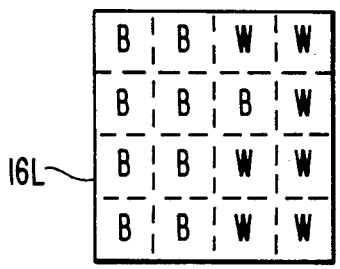
FIG. 3(b-2).
(PRIOR ART)
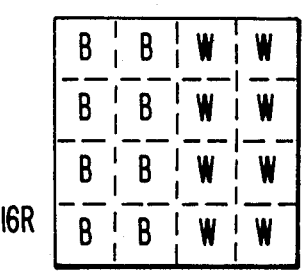
FIG. 3(a-3).
(PRIOR ART)
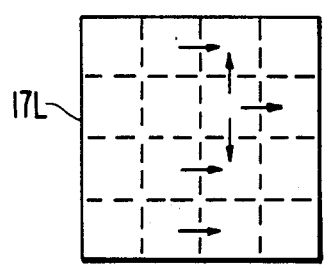
FIG. 3(b-3).
(PRIOR ART)
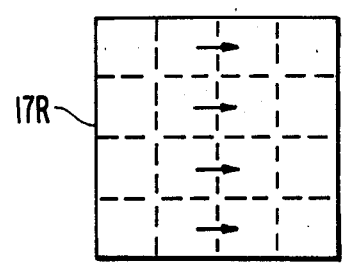

FIG. 4(a-1). (PRIOR ART)
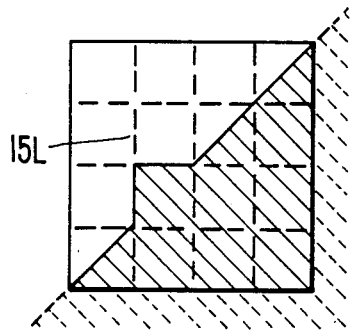
FIG. 4(b-1). (PRIOR ART)
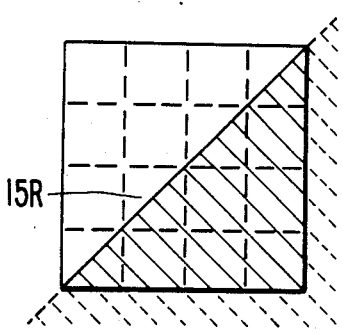
FIG. 4(a-2). (PRIOR ART)
| W | W | W | G |
|---|---|---|---|
| W | W | G | B |
| W | B | B | B |
| G | B | B | B |
16L
FIG. 4(b-2). (PRIOR ART)
| W | W | W | G |
|---|---|---|---|
| W | W | G | B |
| W | G | B | B |
| G | B | B | B |
16R
FIG. 4(a-3). (PRIOR ART)
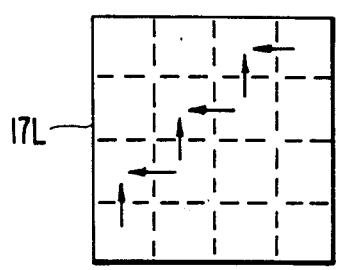
FIG. 4(b-3). (PRIOR ART)
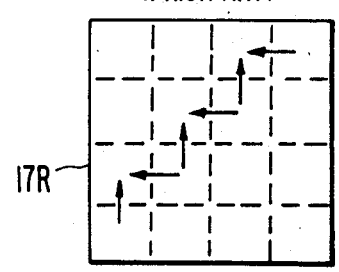

FIG. 5(a-1).
(PRIOR ART)
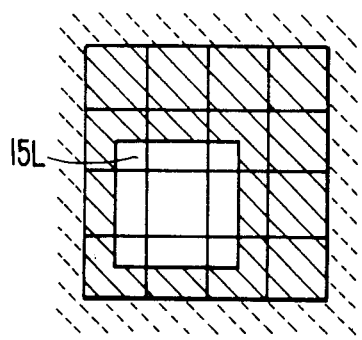
FIG. 5(b-1).
(PRIOR ART)
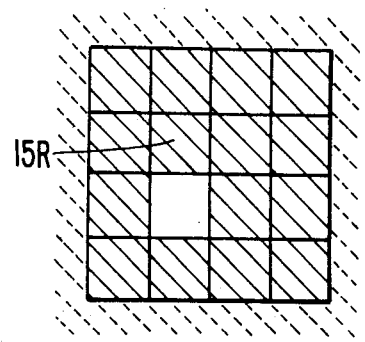
FIG. 5(a-2).
(PRIOR ART)
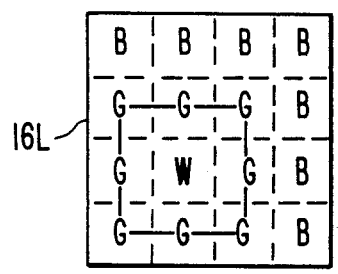
FIG. 5(b-2).
(PRIOR ART)
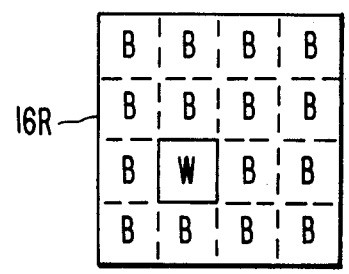
FIG. 5(a-3).
(PRIOR ART)
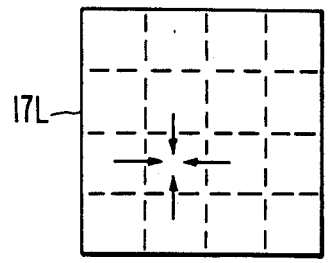
FIG. 5(b-3)
(PRIOR ART)
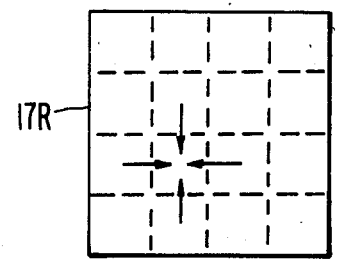

FIG. 7(a-1). 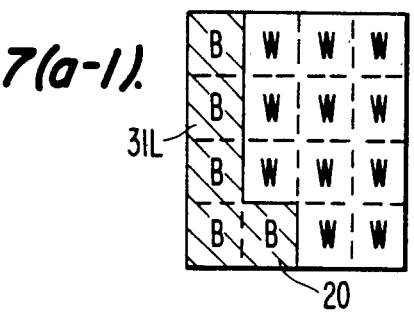
FIG. 7(b-1). 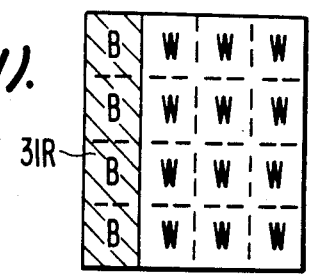
FIG. 7(a-2). 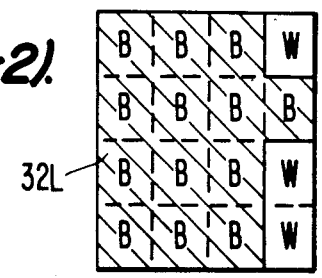
FIG. 7(b-2). 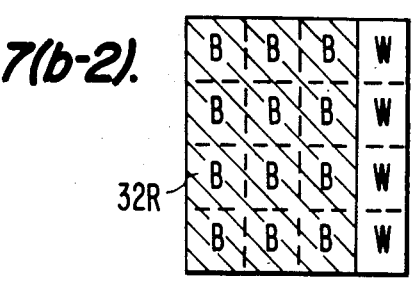
FIG. 7(a-3). 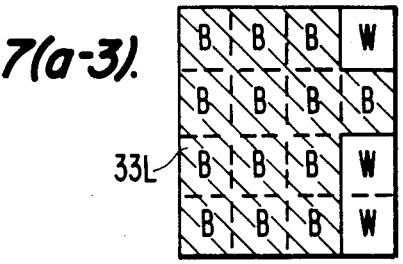
FIG. 7(b-3). 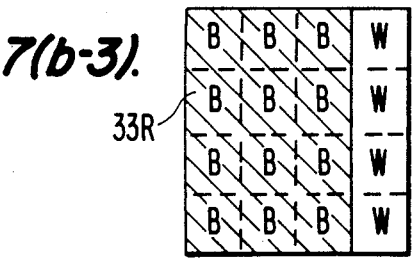
FIG. 7(a-4). 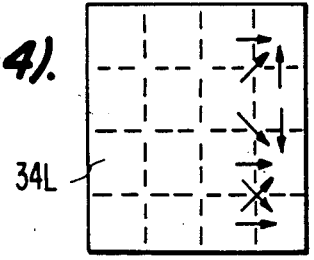
FIG. 7(b-4). 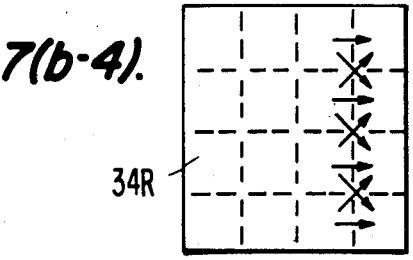

FIG. 8(a-1). 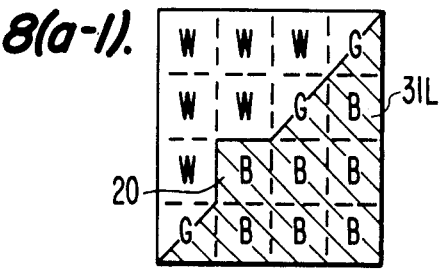
FIG. 8(b-1). 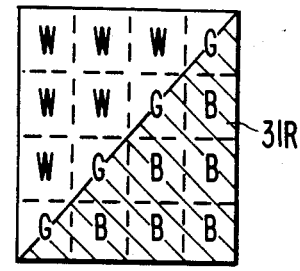
FIG. 8(a-2). 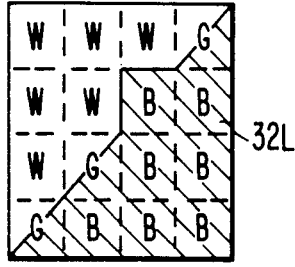
FIG. 8(b-2). 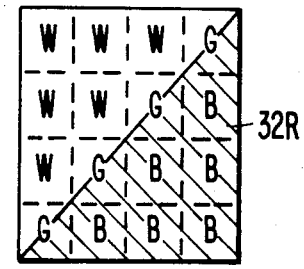
FIG. 8(a-3). 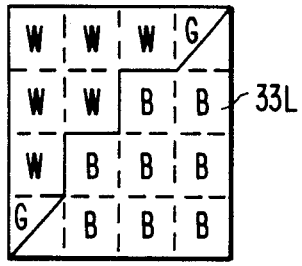
FIG. 8(b-3). 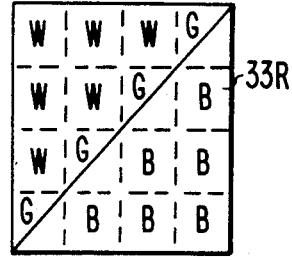
FIG. 8(a-4). 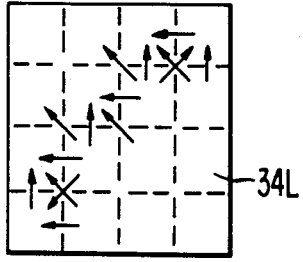
FIG. 8(b-4). 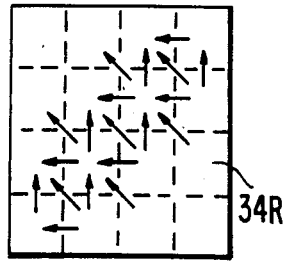

FIG. 9(a-1). 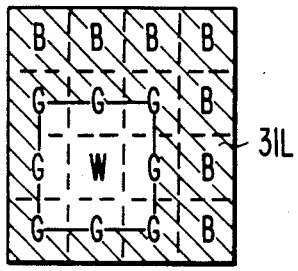
FIG. 9(b-1). 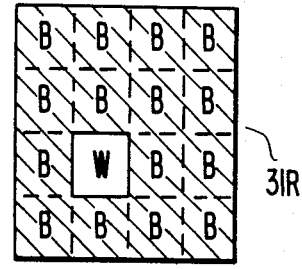
FIG. 9(a-2). 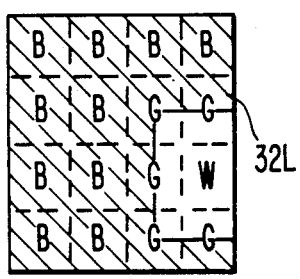
FIG. 9(b-2). 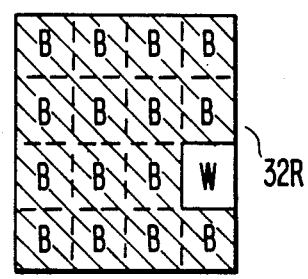
FIG. 9(a-3). 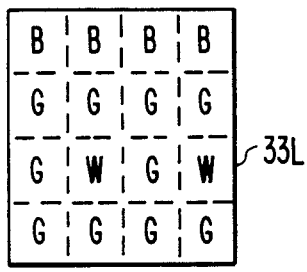
FIG. 9(b-3). 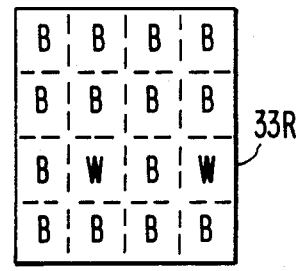
FIG. 9(a-4). 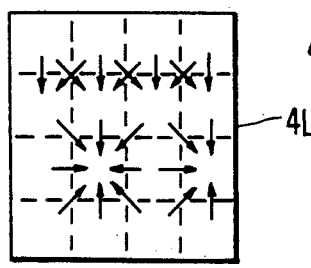
FIG. 9(b-4). 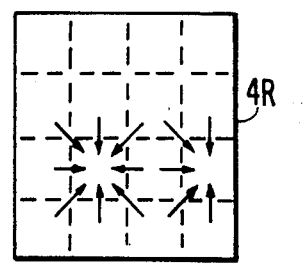

INSPECTING METHOD AND APPARATUS FOR PHOTOMASK PATTERN

BACKGROUND OF THE INVENTION

The present invention relates to an inspecting method and apparatus for a photomask pattern applied to the fabrication of a semiconductor device such as a large semiconductor integrated circuit.

A photomask pattern generally consists of a plurality of patterns, so called "unit patterns", each having the same shape and size for efficient fabrication of a plurality of semiconductor devices on a semiconductor slice by a printing process. The inspecting object of the present invention is such a photomask pattern consisting of a plurality of unit patterns.

A pattern inspection can be classified into two categories: a database comparing method, and a pattern comparing method. In a database comparing method, a unit pattern is compared with its design data, while in a pattern comparing method one unit pattern is compared with another unit pattern having the same shape and size.

Recently, semiconductor devices have become so complex with increases in packing density, that the database comparing method requires a lot of inspecting time and covers a lot of design data. Therefore, the pattern comparing method is preferable to the database comparing method for inspection of a complex photomask pattern.

The pattern comparing method can be also classified into two categories: an analog comparing method, and a digital comparing method. The digital comparing method is essentially preferable with respect to its accuracy, and is becoming popular because recently the digital technology has been advanced and its cost has lowered.

The digital pattern comparing method is performed as follows: (1) a pair of parts, assumed to have the same shape and size, in two unit patterns are selected by two respective optical systems; (2) the two optical images of the parts obtained by the respective optical systems are converted into two groups of analog video signals by respective image sensors in the optical systems; (3) the two groups of analog video signals are respectively digitized into two groups of digital video signals; (4) the two groups of digital video signals are stored as two groups of pattern data in two respective image memories, each having a memory matrix in which memory elements are arranged in correspondence to the arrangement of the picture elements in each optical image with the resolution required for the inspection; and (5) the two groups of pattern data are compared to each other.

The photomask is mounted on a stage to be inspected. The selection of the two unit patterns to be compared can be made by repeatedly shifting the stage in steps and the two optical images can be simultaneously obtained by scanning the stage.

The digital comparing method has the following advantage in comparison with the analog comparing method, the influence of electric noise caused by shifting or scanning the stage can be avoided. However, the digital comparing method also has a disadvantage in that it requires a lot of time for data processing; it takes as much as several times as long as with analog comparing method.

To improve this disadvantage, new technology for the digital comparing method called a "vector comparing method" has been developed and actually used. For example, the method is used in a photomask inspecting apparatus called "KLA 100 or 200 series" which is manufactured by the "KLA Corporation" in the U.S.A. The vector comparing method is derived from the concept that the difference between the data arrangements in two groups of pattern data can be treated as a comparing subject with the application of a vector means. Therefore, in the vector comparing method, it is not necessary to compare the pattern datum in every element of the image memory matrix, thus the data processing time can be shortened.

The vector comparing method is considered to be a very excellent method because of its high accuracy, high sensitivity, and short processing time, however, it has been found that there is a problem in that some kinds of defects in the pattern can not be detected. The present invention intends to solve this problem. Before disclosing the present invention, the prior art vector comparing method and its problems will be discussed.

FIG. 1 is a block diagram of an apparatus for vector comparing inspection of the prior art. In the figure, a photomask 1 is mounted on a stage 100 and light 3 is irradiated from beneath the photomask 1 so that two parts, one in each of two unit patterns, can be detected, one by a left optical system 201 and the other by a right optical system 202. The left and right optical systems 201 and 202 respectively consist of lens systems 211 and 212 and image sensors 41 and 42. Each of the image sensors 41 and 42 consists of linear arrayed sensor elements and each element corresponds to a picture element of the unit pattern which provides sufficient resolution to meet the requirements of the inspection. Each group of video signals from the image sensor 41 and 42 is produced by scanning the stage 100 in a direction perpendicular to the arrayed direction of the image sensor. The distance between the optical system 201 and 202 is adjusted so that the optical images of corresponding parts in each of two unit patterns can be compared. The sequential comparison between corresponding portions of two unit patterns can be made by repeatedly by shifting the stage 100 in steps. The above scan and shift of the stage 100 are controlled by a controller 11. The two groups of analog video signals from the image sensors 41 and 42 are sent to an amplitude distributor 5 in which the two groups of analog video signals are respectively converted into two groups of digital video signals so that the amplitude of each analog video signal is distributed into three levels such as white (W), gray (G), and black (B) corresponding to the amplitude being low, medium, and high. In the three levels, the level G is provided to protect the occurrence of a false error. For example, when the amplitude of the analog signal is in a middle region, if there was no G level, the digital video signal would have to be either B or W; this would product a false error. The level G provides a margin to prevent a false error occurrence. The two groups of digital video signals are stored as pattern data in a first left memory 12L and a first right memory 12R by left and right write-in units 71 and 72 respectively, under the control of the controller 11.

When a photomask pattern is constructed with very high packing density, a minimum area as small as 0.5 ($\mu$m)$\times$0.5 ($\mu$m) is required for the inspection resolution of the photomask pattern. If the linear arrayed image sesor consists of as much as 512 sensing elements and the stage 1 scans a distance corresponding to 512 sensing elements, the optical image created is formed by 512×512 elements at the image plane of the optical system. This is equivalent to the size 256 (μm)×256 (μm) on the photomask 1, and this is the area of a comparing part in the unit pattern.

To store the above pattern data, each memory matrix in first left and the right memory 12L and 12R has 512×512 matrix elements. However, a quantity of pattern data as large as 512×512 matrix elements is too large to be inspected simultaneously with high accuracy, so that the pattern data of 512×512 matrix elements in each of the first memories 12L and 12R are separated to a set of 4×4 matrix elements and stored respectively into a second left memory 13L and a second right memory 13R. The separation and memorization are respective performed by a left separator 81 and a right separator 82. The separated data become the subject of the vector comparing inspection and this separation and memorization are sequentially advanced every time the inspection of the separated data is completed.

One of the signals W, G, and B exists as a pattern datum in each matrix element of each second memory 13L or 13R; therefore a vector can be applied to the boundary between the neighboring elements. In the prior art, the vector is provided in four directions; left, right, up, and down with equal magnitude, and the direction is determined by the following definition: when the datum B and W are adjcently arranged along longitude or latitude, the vector direction is defined from B to W; when the datum G is surrounded by the data W in all four primary directions, four vectors from G to W are provided along longitude and latitude; when the datum G is surrounded by the data B in all four primary directions, four vectors from B to G are provided along longitude and latitude; and when the data are arranged like B-G-W in longitude or latitude, G is changed to B so that only one vector from the changed B to W is provided. Thus, in the prior art, a vector can be provided along longitude and latitude, but can not be provided along a diagonal.

These vectors are generated by a left vector generator 91 and a right vector generator 92, and the vector data are respectively fed to a left vector memory 14L and a right vector memory 14R in a vector memories 14. The vector data in the vector memory 14L and 14R are compared by a vector comparator 10 in every vector direction. For example, if there is a right directional vector in the left memory and no right directional vector in the right memory, the comparator 10 outputs the information that there is a defect; if there are two right directional vectors in the left memory and a right directional vector in the right memory, the comparator 10 outputs the information that there is no defect. Thus, the comparator 10 does not care about the total number of respective directional vectors in each memory, the comparator 10 only compares whether there are vectors having the same direction in the left and the right memory.

FIG. 2 is a flow chart for the prior art inspecting apparatus illustrated in FIG. 1. Reference numerals in FIG. 2 are the same as the block numerals in FIG. 1 to indicate where the function of the blocks exist. In addition, a stage coordinate memory 300 and an inspection output device 400 are included in FIG. 2. When the vector comparator 10 produces a "NO" signal, this means there is no defect, and the signal is fed back to the separators 81 and 82 to advance the inspection of the next separated pattern; when the vector comparator 10 produces a "YES" signal, this means there is a defect and the stage coordinate memory 300 records the stage position at which there is a defect. After the recording the position, the stage coordinate memory 300 advances the separator 81 and 82 to inspect the next separated pattern. When the inspection of the whole photomask pattern is finished, a human inspector can check the inspection results by observing the stored data in the stage coordinate memory 300 on the inspection output device 400 such as a cathode-ray tube or a sheet of printed paper.

FIG. 3 illustrates how to perform the prior art vector comparing inspection, showing an example of a defect on the photomask pattern. In FIG. 3, FIGS. 3(a-1) and 3(b-1) depict the optical images, i.e., the parts of the photomask pattern to be compared to each other. FIG. 3(a-1) depicts an optical image corresponding to the separated data in the left second memory 13L and FIG. 3(b-1) corresponds to that in the right second memory 13R. The parts of the oblique dotted lines located outside of the square frame in each figure indicate how the optical image continues in the photomask pattern. A pattern 15L in FIG. 3(a-1) has a defective part 20 and a pattern 15R in FIG. 3(b-1) is assumed to be normal. A data matrix 16L in FIG. 3(a-3) represents the separated data in the left second memory 13L, and a data matrix 16R in FIG. 3(b-2) represents the data in the right second memory 13R. Vector patterns 17L and 17R in FIGS. 3(a-3) and 3(b-3) respectively depict the vector pattern in the left vector memory 14L and the right vector memory 14R. Comparing the vector directions in FIGS. 3(a-3) and 3(b-3), the following results can be obtained: a right vector exists in both memories, a left vector does not exist in either memory, an up vector exists only in the left memory, and a down vector also exists only in the left memory. Therefore, the comparator 10 in FIG. 1 outputs the information that there is a defect in the photomask. Thus, defective part 20 in the separated pattern 15L can be detected by the vector comparing inspection.

The digital pattern datum at the defective part 20 was B in the above example. However, even if the pattern datum is G; that is, defect is as small as the half of the part (matrix element) 20, the same results can be obtained, because the data including the defective part 20 are arranged in B-G-W in latitudinal direction and this arrangement is changed to B-B-W in the vector generator 91. Thus, the vector comparing inspection is effective to detect a very small defect, and further, importantly, the inspection can be performed very quickly because the inspection can be done just by comparing the directions of respective vector data. However, it has been found that this inspection has a problem in that some pattern errors cannot to be detected even though the detected signal has enough amplitude like a datum B when it should be W or G.

FIGS. 4 and 5 illustrate the problems in the vector comparing inspection of the prior art, showing examples of indetectable defects. FIG. 4 shows a defect in a slant pattern. FIG. 5 shows square holes in respective separated patterns; corresponding sides of the square holes are parallel to each other and the shapes are the same, but the sizes are different.

In FIG. 4, the situation of each figure is the same as that in FIG. 3. A separated pattern 15L in FIG. 4(a-1) has a defective part 20 and a separated pattern 15R in FIG. 4(*b*-1) normal. As the pattern appears at a slant in the matrix frame, there are G pattern data at the slant edge of the pattern. So, the data matrices in the separated memories 13L and 13R are as indicated by data matrices 16L and 16R in FIGS. 4(*a*-2) and 4(*b*-2), and the vector patterns in the vector memories 14L and 14R are generated as in FIGS. 4(*a*-3) and 4(*b*-3). A comparison between the vector pattern 17L and 17R, finds the same quantity of the vectors in every direction. This indicates there was no defect on the photomask pattern.

In FIG. 5, the separated pattern data are as indicated in FIGS. 5(*a*-2) and 5(*b*-2). Thus, respective vector patterns are generated as in FIGS. 5(*a*-3) and 5(*b*-3). This result also indicates there was no defect, because the vectors in the left and the right memory are equal in every direction.

The undetected defects in FIGS. 4 and 5 often appear in an inspection of the photomask pattern, for example, the problem of the square holes occurs in the inspection of a contact hole in a large scale integrated circuit, and it is very important for the vector comparing methods to detect such defects if it is to be used with confidence.

SUMMARY OF THE INVENTION

Therefore, an object of the present invention is to improve a prior art vector comparing method for the photomask pattern inspection so that a defects which have been impossible to be detected by the prior art method can detect using a vector comparing method and its apparatus according to the present invention.

The present invention can be performed by the following steps. First, shifting pairs of separated data, which are separated from pairs of pattern data of respective optical images obtained from the photomask pattern by optical systems and stored in respective separated data memories, a proper equal amount of memory element to provide a pair of shifted data. Second, synthesizing the pairs of separated data and shifted data with a logical calculation following either black or white priority logic to provide a pair of synthesized data. Third, storing the pairs of synthesized data in respective synthesized data memories. Fourth, generating vectors from the data arrangements in the respective synthesized memories in latitudinal, longitudinal, and diagonal directions using relations among black, gray and white datums. Fifth, storing the vectors in a pair of vector memories. Sixth summing the quantity of the vectors having the same direction in each of the vector memories. Seventh, comparing between respective vector summations to detect differences between the summations. Eighth, and producing information about a defect in the photomask pattern if there is a difference in any comparison.

Applying the present invention to the vector comparing method and its apparatus of the prior art, any kind of defect in the photomask pattern can be detected with high accuracy, high sensitivity, and at high speed.

BRIEF DESCRIPTION OF THE DRAWINGS

FIG. 3 is how the drawing illustrating a vector comparing inspection process of the prior art finds a defect on a photomask pattern;

FIG. 4 is a drawing illustrating the prior art vector comparing method as applied to another defect on a photomask pattern;

FIG. 5 is a drawing illustrating the prior art vector comparing method as applied to still another defect on a photomask pattern;

FIG. 7 is a drawing illustrating how an embodiment of a process for a vector comparing inspection of the present invention detects a defect on a photomask pattern;

FIG. 8 is a drawing illustrating how another embodiment of a process for a vector comparing inspection of the present invention detects another defect on a photomask pattern;

FIG. 9 is a drawing illustrating how still another embodiment of a process for a vector comparing inspection of the present invention detects still another defect on a photomask pattern;

DETAILED DESCRIPTION OF THE INVENTION

Figure 6:
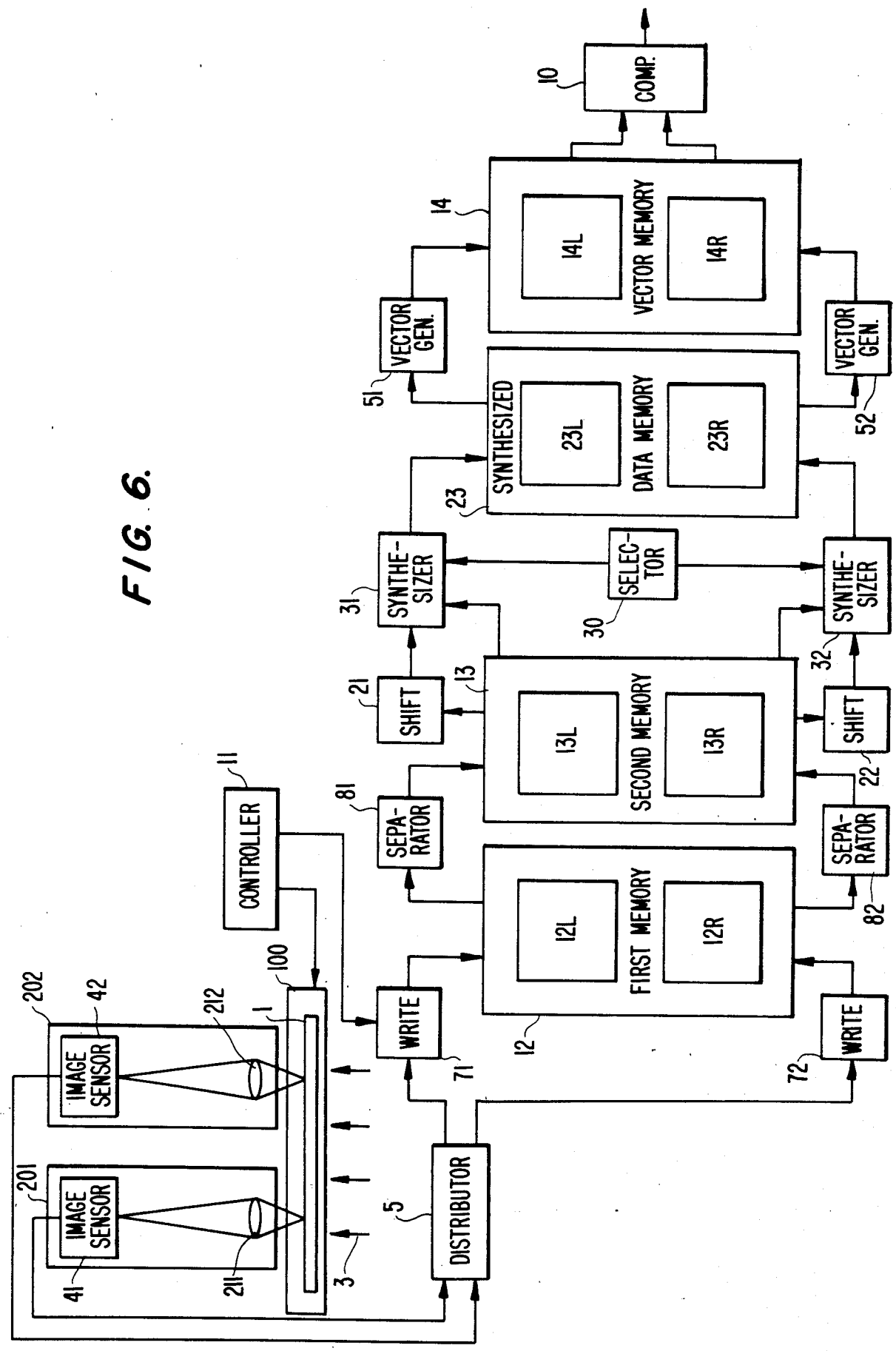
FIG. 6 is a block diagram of an embodiment for a photomask inspecting apparatus applying a vector comparing method of the present invention.

FIG. 6 is a block diagram of an embodiment for a photomask inspecting apparatus applying a vector comparing method of the present invention. In FIG. 6, the reference characters which are the same as in FIG. 1 refer to units having the same function as in FIG. 1, and the following units are added. Left and right data shifts 21 and 22 shift the separated data in respective left and right second memories 13L and 13R a proper amount along longitude and latitude and thus provide a pair of shifted data. The proper amount is previously decided by the inspector based on information about the photomask pattern to be inspected.

Left and right data in the second left and right memories, 13L and 13R respectively, synthesizers 31 and 32 synthesize the shifted data and the original separated data providing a pair of synthesized data. In the synthesis, the following data calculations must be considered: B+B, B+G, B+W, G+G, G+W, and W+W. These can be made by following one of at least two logical calculations, one is "B priority logic" and the other is "W priority logic":

|       | B priority logic | W priority logic |
| ----- | ---------------- | ---------------- |
| B + B | B                | B                |
| B + G | B                | G                |
| B + W | B                | W                |
| G + G | G                | G                |
| G + W | G                | W                |
| W + W | W                | W.               |

This B/W selection is also made by the inspector, operating a logic selector 30 before starting the inspection, based on the information about the photomask pattern to be inspected. A synthesized data memory 23 comprising a left synthesized data memory 23L and a right synthesized data memory 23R stores the above synthesized data.

Figure 1:
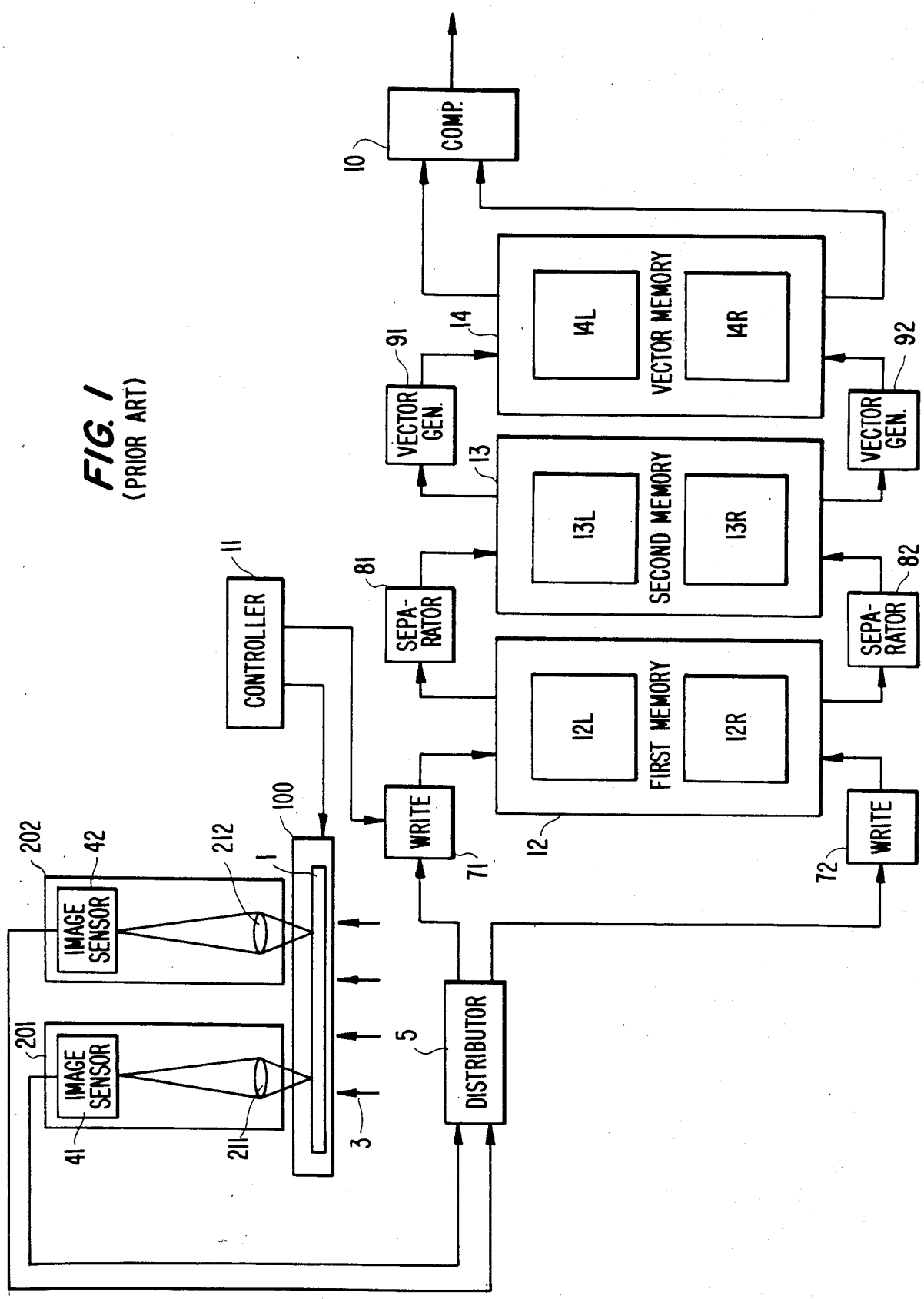
FIG. 1 is a block diagram of a photomask inspecting apparatus applying a vector comparing method of the prior art.

Left and right vector generators 51 and 52 are similar to the vector generators 91 and 92 in FIG. 1, but the following two functions are added. First, a new treatment of the datum G is provided. A vector is provided for neighboring (adjacent) data B-G and G-W. A vector from B for G is provided to the arrangement B-G and a vector from G to W is provided for the arrangement G-W. Second, vectors along diagonals are provided; therefore, eight vector directions can be used in total.

The functions of these additional units will be more concretely explained with reference to FIGS. 7, 8, and 9. FIG. 7 illustrates how the embodiment of FIG. 6 inspects a photomask pattern using a method according to the present invention. The same separated patterns are used in FIG. 7 as were used in FIG. 3. FIGS. 7(a-1) and 7(b-1) depict the separated data stored in the respective second memories 13L and 13R. Thick solid lines indicate the respective separated patterns in which pattern 13L has a defective part 20 and pattern 31R is normal. These separated pattern data are respectively shited by the data shifters 21 and 22. In the example illustrated in FIG. 7, the shift amount was selected to shift two matrix elements towards the right and two elements up in the matrix of each second memory, resulting in the patterns represented by reference characters 32L and 32R in FIG. 7(a-2) and in FIG. 7(b-2) respectively. FIGS. 7(a-2) and 7(b-2) are only for explanation, they do not actually exist in any of the memories. The original pattern data 31L and the shifted pattern data 32L, and the data 31R and 32R are respectively synthesized, to form respective new patterns. A logical calculation using "B priority logic" will be applied in this case. Thus, the synthesized data are represented by 33L and 33R in respective FIGS. 7(a-3) and 7(b-3). The synthesized data are stored in the synthesized data memory 23, i.e., the left and right synthesized data memories 23L and 23R, respectively. The left and right vector generators 51 and 52 generate the vectors from respective synthesized data, so that the generated vectors are as represented by 34L and 34R in respectively FIGS. 7(a-4) and 7(b-4). These vectors are respectively stored in the left and right vector memories 14L and 14R in the vector memory 14. The vector comparator 10 compares the summation of respective vectors in the vector memories 14L and 14R. The differences in respective vectors in the eight directions are as follows: up—1, down—1, right—1; diagonal (from left-up to right-down)—1; diagonal (from left-down to right-up)—1; and the rest are all zero. Therefore, the vector comparator outputs the information that the photomask has a defect. In the above comparison, there are differences in five of the directions, however, any one of these is enough to make the vector comparator 10 produce information indicating a defect. The defect in the separated data mentioned above can also be detected by the prior art apparatus; however, the defects which will be described with reference to FIGS. 8 and 9 which are the same as FIGS. 4 and 5, respectively, can not be detected by the prior art technology.

In FIG. 8, FIGS. 8(a-1) and 8(b-1) depict the separated data stored in the second memories 13L and 13R, respectively. A pattern 31L has a defective part 20 and a pattern 31R is normal. FIGS. 8(a-2) and 8(b-2) depict the shifted pattern data; the shift amount is one matrix element right and up. FIGS. 8(a-3) and 8(b-3) show respective synthesized data; the synthesis is made under the condition of "B priority logic". From the synthesized data, respective vector signals can be obtained as shown by FIGS. 8(a-4) and 8(b-4). The vector comparator 10 compares the summation of respective vectors in the vector memories 14L and 14R. The differences in the respective vectors in the eight directions are as follows: up—2, left—2, diagonal (from right-down to left-up)—2, diagonal (from left-down to right-up)—1, diagonal (from right-up to left-down)—1, and the rest are all zero. Therefore, the vector comparator 10 outputs the information that the photomask has a defect.

In FIG. 9, FIGS. 9(a-1) and 9(b-1) show the separated data stored in the second memory 13. In the separated patterns, the square holes in pattern 31L and 31R should be the same in shape and size, but actually they are not the same size. FIGS. 9(a-2) and 9(b-2) show respective shifted data; the shift amount is two matrix elements towards the right. FIGS. 9(a-3) and 9(b-3) show the synthesized data; each synthesis is made under the condition of "W priority logic". From the synthesis data, respective vectors are provided as shown by FIGS. 9(a-4) and 9(b-4). The vector comparator 10 compares the summation of respective vectors in the vector memories 14L and 14R. The differences in the respective vectors in the eight directions are as follows: down—4, diagonal (from left-up to right-down)—3, diagonal (from right-up to left-down)—3, and the rest are all zero. Therefore, the vector comparator 10 outputs the information that the photomask has a defect.

In the above explanation, the determination of the shift amount and the selection of the B/W priority logic can be performed by an inspector skilled in the art of photomask inspection. However, if the photomask inspection is required to be performed without an inspector's assistance, proper inspection can be performed by providing the software or hardware to sequentially perform several inspections selecting different shit amounts and B/W priority logic. If a short inspecting time is required, this can be met by providing parallel data shifters, each having a proper shift amount, along with data synthesizers. Thus, there would be many inspection outputs simultaneously, and if one of the outputs produces the information of a defect, it can be indicated that the photomask has a defect.

Furthermore, the slicing levels which provide the digital data B, G, and W in the amplitude distributor 5 and the shift amount set in the data shifters 21 and 22 can be selected properly considering the shape of the pattern or the size of the defect to be inspected. In the comparator 10, the detection sensitivity can be changed, considering the features of the pattern to be inspected, by adjusting a threshold amount of vector difference which will produce the output of a defect. This is to avoid the occurrence of a false error.

Figure 2:
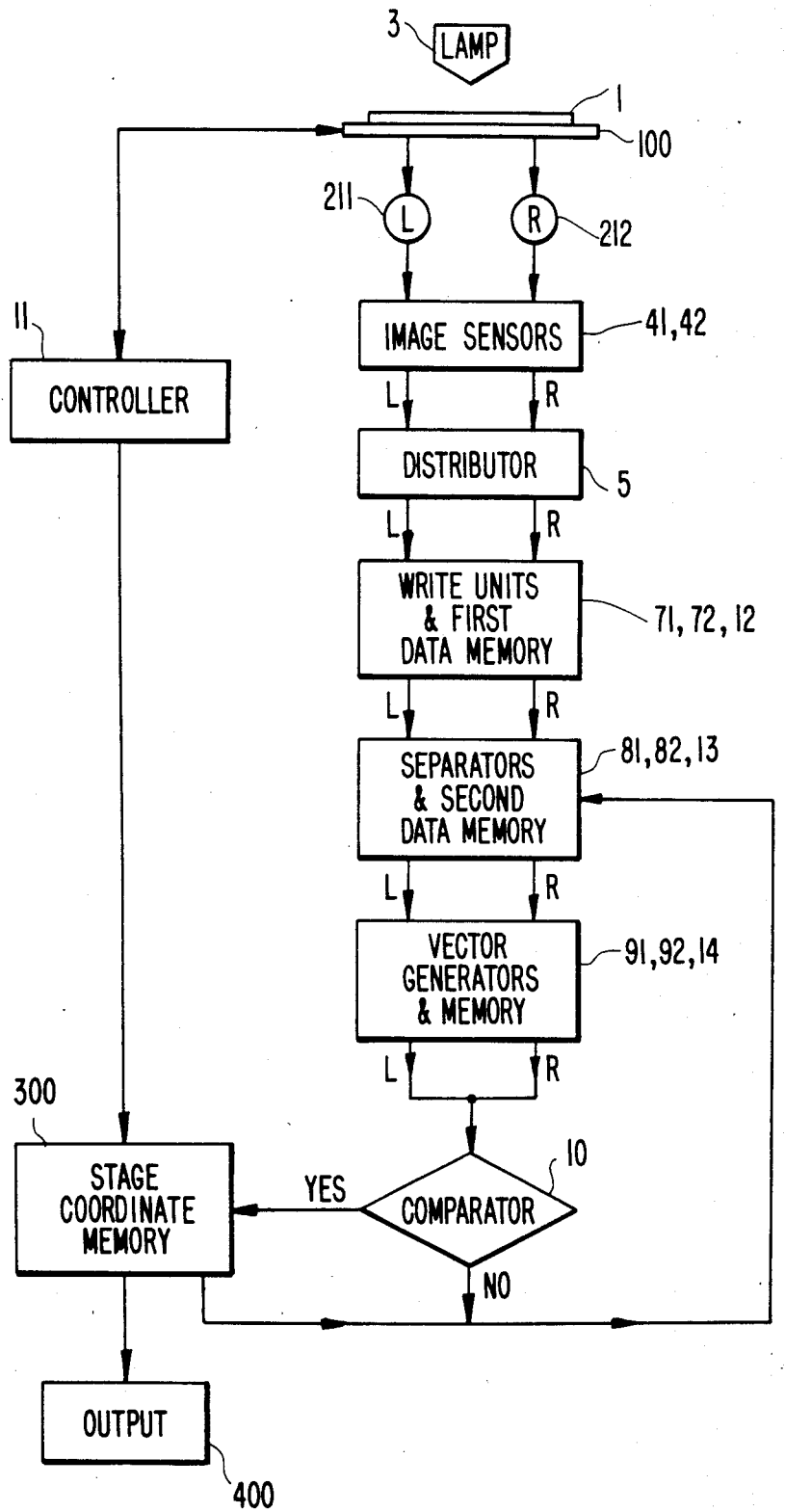
FIG. 2 is a flow chart for the photomask inspecting apparatus illustrated in FIG. 1, applying the vector comparing method of the prior art.
Figure 10:
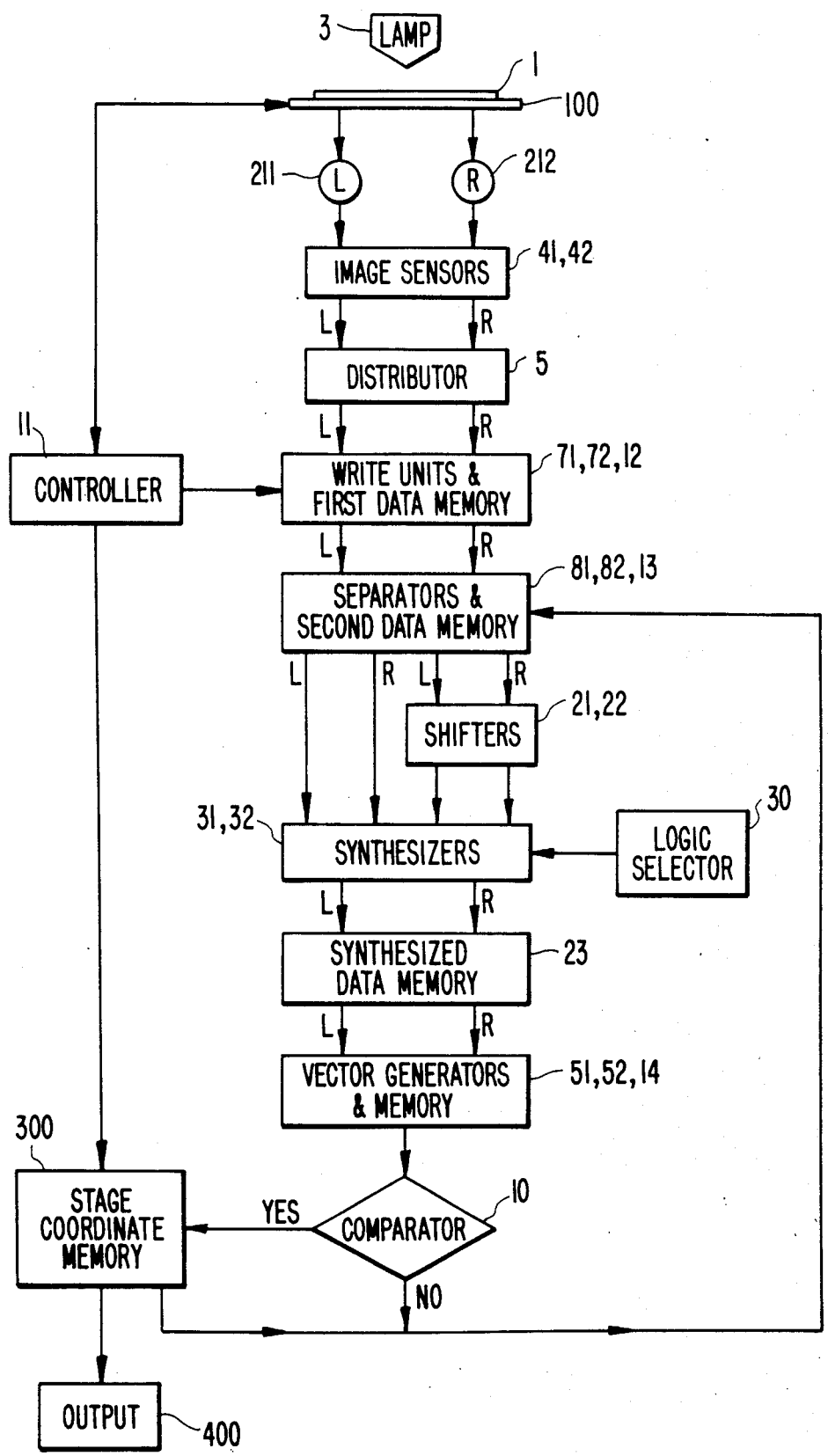
FIG. 10 is a flow chart for the embodiment of the photomask inspecting apparatus applying the vector comparing method of the present invention illustrated in FIG. 6.

FIG. 10 is a flow chart for the inspecting apparatus of the present invention shown in FIG. 6. The same reference numerals are used in FIG. 10 as in FIG. 6, and reference numerals 300 and 400 are the same as in FIG. 2. The data shifter 21 and 22 in FIG. 10 shift the data in the second memory 13.

Figure 11:
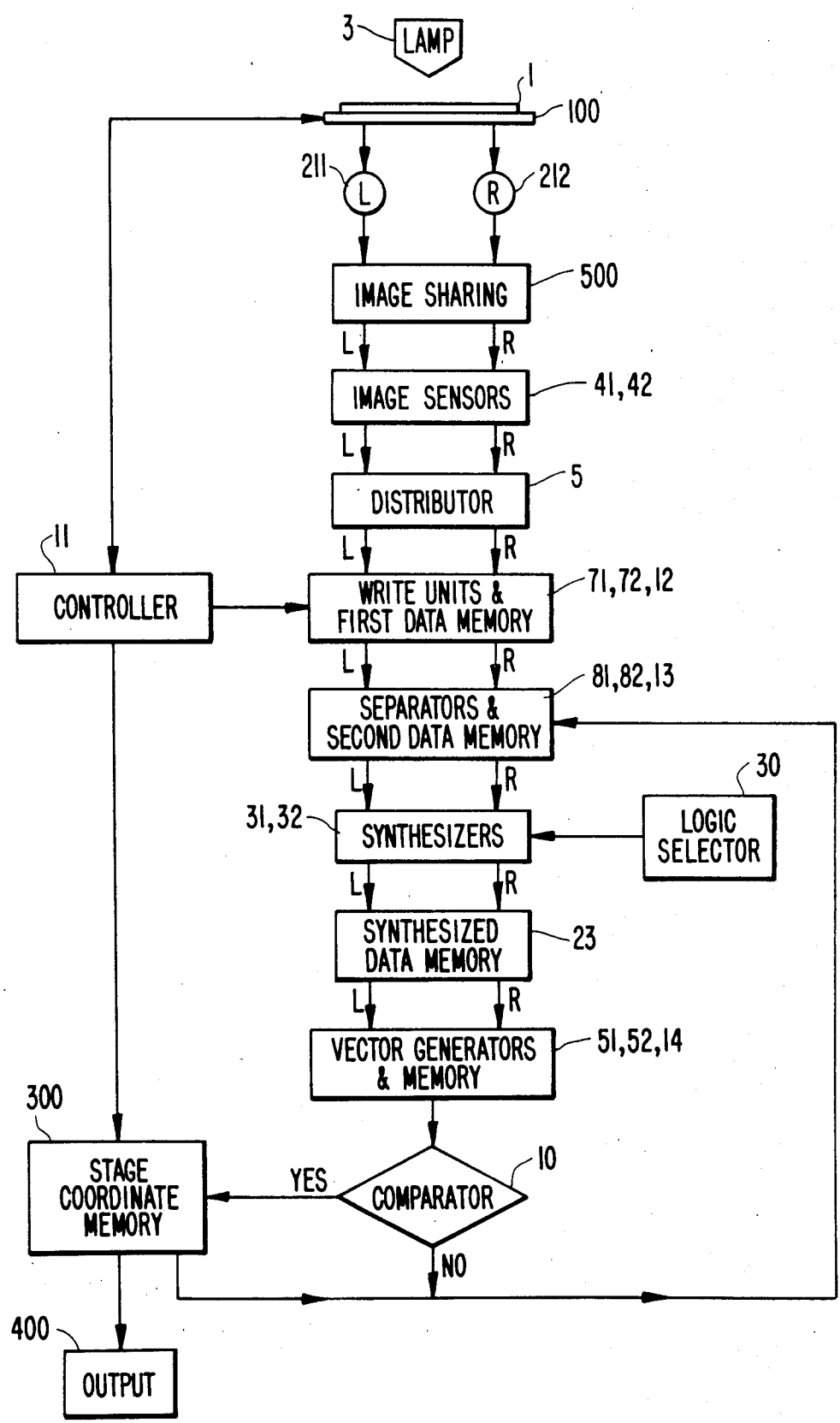
FIG. 11 is a flow chart for another embodiment of a photomask inspecting apparatus applying a vector comparing method of the present invention.

The data shifting can also be provided by the optical system; this type of shifting is called image sharing. FIG. 11 is a flow chart applying image sharing. Reference numeral 500 respects a block for the image sharing device. In this case, the image sharing is performed to provide the data in the second data memory 13 and the data synthesizer 31 and 32 of FIGS. 6 and 10.

As mentioned with respect to FIGS. 8 and 9, the defects in a photomask pattern which have been impossible to detect by the prior art technology can be detected by the present invention.

What is claimed is:

1. An inspection method for a photomask pattern applying a vector comparing method, comprising the steps of:
   (a) obtaining a pair of optical images, which are to be compared, from the photomask pattern;
   (b) converting the pair of optical images into two groups of electrical analog signals;
   (c) distributing the two groups of electrical analog signals into two groups of digital data, each of the two groups of digital data comprising a first number of matrix elements represented by datums having a value representing one of black, gray and white in accordance with high, middle, and low amplitudes, respectively, of a corresponding analog signal in one of the two groups of electrical analog signals;
   (d) separating two groups of separated data from the two groups of digital data, sequentially and respectively, each of the two groups of separated data having a second number of matrix elements, the second number being less than the first number of matrix elements in each of the two groups of digital data;
   (e) shifting the two groups of separated data respectively by a shift amount of at least one matrix element of each of the two groups of separated data in at least one of a latitudinal and longitudinal direction to provide at least two groups of shifted data;
   (f) synthesizing the two groups of separated data and the at least two groups of shifted data, respectively, to provide at least two groups of synthesized data;
   (g) generating vectors from arrangements of the at least two groups of synthesized data to provide at least two groups of vectors, each of the two groups of vectors comprising at least one of:
   a first vector from one of the datums representing black to an adjacent datum representing white, the first vector having a direction in one of latitudinal, longitudinal, and diagonal directions,
   a second vector, having one of the directions, from one of the datums representing black to an adjacent datum representing gray, and
   a third vector, having one of the directions, from one of the datums representing gray to an adjacent datum representing white, the first, second and third vectors having equal magnitude;
   (h) summing amounts of vectors in each of the directions for each groups of vectors;
   (i) comparing the amounts summed in step (h), respectively in each of the directions, for the at least two groups of vectors, to provide differences between the amounts; and
   (j) producing an output that indicates the photomask pattern has a defect when any one of the differences is non-zero.

2. An inspecting method according to claim 1, wherein the shift amount is provided by a step of (k) pre-inspecting the photomask patterns.

3. An inspecting method according to claim 1, wherein the values of the datums are calculated logically by following one of a black priority logic and a white priority logic in said synthesizing of step (f), as follows, where black, gray and white are represented by B, G, and W, respectively:

|       | B priority logic | W priority logic |
|-------|------------------|------------------|
| B + B | B                | B                |
| B + G | B                | G                |
| B + W | B                | W                |
| G + G | G                | G                |
| G + W | G                | W                |
| W + W | W                | W                | the one of black and white priority logic also being provided by said pre-inspecting of the photomask pattern.

4. An inspecting apparatus using a vector comparing method, comprising:
   a pair of optical systems, each comprising a lens system coupled to an image sensor, said optical systems respectively obtaining optical images from respective parts of the photomask pattern and converting the optical images into two groups of electrical analog signals;
   an amplitude distributor, operatively connected to said image sensors, for distributing the two groups of electrical analog signals respectively into two groups of digital data;
   two first memories, operatively connected to said amplitude distributor, respectively, for storing the two groups of digital data;
   two data separators, operatively connected to said two first memories, respectively for separating two groups of separated data from the two groups of digital data;
   two second memories, operatively connected to said two data separators, respectively, for storing the two groups of separated data;
   two data shifters, operatively connected to said two second memories, respectively, for providing two groups of shifted data;
   two data synthesizers, operatively connected to said two second memories, respectively, for providing two groups of synthesized data by logical calculations;
   a logic selector, operatively connected to said two data synthesizers, for selecting one of black priority logic and white priority logic for the logical calculations in said two data synthesizers;
   two synthesized data memories, operatively connected to said two data synthesizers, respectively for storing the two groups of synthesized data;
   two vector generators, operatively connected to said two synthesized data memories, respectively, for generating two groups of vectors;
   two vector memories operatively connected to said two vector generators, respectively, for storing the two groups of vectors, each vector having a direction; and
   vector comparator means, operatively connected to said vector memories, for providing summations in each direction of the vectors stored in each of said two vector memories, for comparing the summations of each of said two vector memories, for providing differences between the summations of each of said two vector memories, and for producing output informing of a defect in the photomask pattern if a non-zero difference is obtained as at least one of the differences.

5. An inspecting apparatus using a vector comparing method, comprising:
- two optical systems, each comprising a lens system coupled to an image sensor, said optical systems respectively obtaining optical images from respective parts of the photomask pattern and converting the optical images into two groups of electrical analog signals;
- an amplitude distributor, operatively connected to said image sensors, for distributing the two groups of electrical analog signals into two groups of digital data;
- two first memories, operatively connected to said amplitude distributor, respectively, for storing the two groups of digital data;
- two data separators, operatively connected to said two first memories, respectively, for separating two groups of separated data from the two groups of digital data;
- two second memories, operatively connected to said two data separators, respectively, for storing the two groups of separated data;
- two groups of data shifters, operatively connected to said two second memories, respectively, for simultaneously providing two groups of shifted data by using a plurality of shift amounts to form the two groups of shifted data from the two groups of separated data;
- two groups of pairs of data synthesizers, operatively connected to said two groups of data shifters and said two second memories, respectively, for simultaneously providing two groups of pairs of synthesized data, one of each of the pairs of synthesized data being synthesized by logical calculations using black priority logic and the other of each of the pairs of synthesized data being synthesized using white priority logic;
- a logic generator, operatively connected to said two groups of pairs of data synthesizers, for generating the black priority logic and the white priority logic for the logical calculations in said two groups of pairs of data synthesizers;
- two groups of pairs of synthesized data memories, operatively connected to said two groups of pairs of data synthesizers, respectively, for simultaneously storing the two groups of pairs of synthesized data;
- two groups of pairs of vector generators, operatively connected to said two groups of pairs of synthesized data memories, respectively, for simultaneously providing two groups of paired sets of vectors from the two groups of pairs of synthesized data, each vector having a direction;
- two groups of pairs of vector memories, operatively connected to said two groups of pairs of vector generators, respectively, for simultaneously storing the two groups of of paired sets of vectors; and
- vector comparator means, operatively connected to said two groups of pairs of vector memories, for simultaneously providing summations in each direction of the vectors stored in each of said two groups of pairs of vector memories, for comparing the summations to determine whether there is a difference between the summations of the sets of vectors of any pair in the paired sets of vectors, and for producing an output informing of a defect in the photomask pattern if any difference is obtained between the summations compared by said vector comparator means.

6. An inspection method for a photomask pattern applying a vector comparing method, comprising the steps of:
- (a) obtaining from the photomask pattern a pair of optical images, having picture elements, which are to be compared;
- (b) shifting periodically and respectively the optical images by a shifting amount corresponding to an amount of the picture elements in the optical images, the amount of the picture elements being provided by pre-inspection of the photomask pattern;
- (c) repeating steps (a) and (b) periodically to provide a new pair of optical images and a pair of shifted optical images;
- (d) synthesizing each image in the pair of optical images with a corresponding one of the pair of shifted optical images to produce a pair of synthesized images; and
- (e) comparing the pair of synthesized images to detect differences between the pair of optical images.

7. A photomask pattern inspection apparatus, comprising:
- image means for obtaining initial images of corresponding portions of unit patterns in a photomask;
- shift means, operatively connected to said image means, for shifting each of the initial images by a shift amount to obtain shifted images;
- synthesizing means, operatively connected to said image means and said shift means, for synthesizing the initial images and shifted images of the corresponding portions, respectively, to form synthesized images; and
- vector comparison means, operatively connected to said synthesizing means, for generating vectors, having directions, indicating changes in intensity within each of the synthesized images, for comparing the vectors in each of the synthesized images, respectively for each of the directions, and for indicating when at least one difference is detected by the comparing.

8. A method for comparing initial images of corresponding portions of unit patterns in a photomask, comprising the steps of:
- (a) shifting each of the initial images by a shift amount to obtain shifted images;
- (b) synthesizing the initial images and the shifted images of the corresponding portions, respectively, to form synthesized images;
- (c) generating vectors, having directions, indicating canges in intensity within each of the synthesized images;
- (d) comparing the vectors in each of the synthesized images, respectively for each of the directions; and
- (e) indicating when at least one difference is detected by the comparing in step (d).

9. A method according to claim 8,
wherein the initial images, shifted images and synthesized images all are comprised of matrix elements having values representing one of at least black, gray and white, and
wherein step (b) comprises the step of assigning the values to the matrix elements in the synthesized images in dependence upon the values of corresponding matrix elements in the initial images and the shifted images in accordance with one of black priority logic and white priority logic.

10. A method according to claim 9, wherein said assigning in step (b) in accordance with black priority logic comprises the steps of:
   (bi) assigning each of the matrix elements in the synthesized images the value representing black if the value of any of the corresponding matrix elements, corresponding thereto, represents black;
   (bii) assigning each of the matrix elements the value representing gray if the value of any of the corresponding matrix elements, corresponding thereto, represents gray and the value of none of the corresponding matrix elements, corresponding thereto, represents black; and
   (biii) assigning one of the matrix elements of the synthesized image the value representing white if the value of all of the corresponding matrix elements, corresponding thereto, represents white.

11. A method according to claim 9, wherein said assigning in step (b) in accordance with white priority logic comprises the steps of:
   (bi) assigning each of the matrix elements in the synthesized images the value representing white if the value of any of the corresponding matrix elements, corresponding thereto, represents white;
   (bii) assigning each of the matrix elements the value representing gray if the value of any of the corresponding matrix elements, corresponding thereto, represents gray and the value of none of the corresponding matrix elements, corresponding thereto, represents white; and
   (biii) assigning each of the matrix elements of the synthesized image the value representing white if the value of both of the corresponding matrix elements, corresponding thereto, represents white.

12. A method according to claim 8, wherein the directions of the vectors are at least one of up, down, left, right and the four diagonal directions between up and right, right and down, down and left, and left and up.

13. A method according to claim 12, wherein step (d) comprises the steps of:
   (di) summing the vectors in each of the directions in each of the synthesized images to provide a number of vectors in each direction; and
   (di) comparing the number of vectors in each direction for each of the synthesized images.

* * * * *

UNITED STATES PATENT AND TRADEMARK OFFICE
CERTIFICATE OF CORRECTION

PATENT NO. : 4,669,123      Page 1 of 2

DATED : May 26, 1987

INVENTOR(S) : Kobayashi et al.

It is certified that error appears in the above-identified patent and that said Letters Patent is hereby corrected as shown below:

Front page [57] ABSTRACT, line 21, "vectors" should be
--each of the groups of synthesized data--;

Col. 2,   line 34, delete "the" (second occurrence);
          line 43, delete "by" (second occurrence);
          line 58, "product" should be --produce--;
          line 68, "sesor" should be --sensor--.

Col. 3,   line 46, "memories" should be --memory--;
          line 47, "memory" should be --memories--.

Col. 4,   line 5, delete "the";
          line 27, "3(a-3)" should be --3(a-2)--;
          line 45, "defect" should be --the defect--;
          line 45, delete "the" (first occurrence).

Col. 5,   line 21, "methods" should be --method--;
          line 26, "the" should be --a--;
          line 27, "a" should be --the--;
          line 37, "element" should be --elements--;
          line 51, delete "and";
          line 66, "how the" should be --a--;
          line 66, "a" should be --how the--.

UNITED STATES PATENT AND TRADEMARK OFFICE
CERTIFICATE OF CORRECTION

PATENT NO. : 4,669,123
DATED : May 26, 1987
INVENTOR(S) : Kobayashi et al.

It is certified that error appears in the above-identified patent and that said Letters Patent is hereby corrected as shown below:

Col. 6, line 38, "shifts" should be --shifters--;
      line 45, delete "in the second left and right memo-";
      line 46, delete "ries, 13L and 13R respectively,";
      line 48, "data providing" should be --data in the second left and right memories, 13L and 13R respectively, providing--.

Col. 7, line 7, "for" should be --to--;
      line 8, "to" should be --for--;
      line 21, "13L" should be --31L--;
      line 23, "shited"" should be --shifted--.

Col. 8, line 38, "shit" should be --shift--.

Col. 12, line 54, "canges" should be --changes--.

Signed and Sealed this

Twenty-ninth Day of December, 1987

Attest:

DONALD J. QUIGG

Attesting Officer      Commissioner of Patents and Trademarks